(12) United States Patent
Brinkmann et al.

(10) Patent No.: US 7,910,626 B2
(45) Date of Patent: Mar. 22, 2011

(54) USE OF S1P RECEPTOR AGONISTS IN HEART DISEASES

(75) Inventors: Volker Brinkmann, Freiburg (DE); Gilles Feutren, Mulhouse (FR); Robert Paul Hof, Gelterkinden (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/244,422

(22) Filed: Oct. 2, 2008

(65) Prior Publication Data

US 2009/0029922 A1 Jan. 29, 2009

Related U.S. Application Data

(63) Continuation of application No. 10/521,297, filed as application No. PCT/EP2003/008085 on Jul. 23, 2003, now abandoned.

(30) Foreign Application Priority Data

Jul. 24, 2002 (GB) .................................. 0217152.8

(51) Int. Cl.
*A01N 33/02* (2006.01)
*A61K 31/135* (2006.01)

(52) U.S. Cl. ..................... 514/646; 514/653; 558/169
(58) Field of Classification Search ................... 514/183
See application file for complete search history.

(56) References Cited

U.S. PATENT DOCUMENTS 6,004,565 A 12/1999 Chiba et al.
2002/0037895 A1 3/2002 Baenteli et al.

FOREIGN PATENT DOCUMENTS

| EP | 0 627 406 | 12/1994 |
|---|---|---|
| EP | 1 002 792 | 5/2000 |
| EP | 1 201 236 | 5/2002 |
| WO | 02/18395 | 3/2002 |
| WO | 03/020313 | 3/2002 |
| WO | 02/064616 | 8/2002 |
| WO | 02/076995 | 10/2002 |

OTHER PUBLICATIONS

Mazurais et al., "Cell Type-Specific Localization of Human Cardiac SIP Receptors," J. Histochem. Cytochem., vol. 50, No. 5, p. 661-669 (2002).
Hwang et al., "FTY720, a New Immunosuppressant, Promotes Long-Term Graft Survival and Inhibits the Progression of Graft Coronary Artery Disease in a Murine Model of Cardiac Transplantation," Circulation, vol. 100, No. 12, pp. 1322-1329 (1999); CAPLUS 1999:658439.
Miyamato et al., Therapeutic Effects of FTY720, a New Immnunosuppressive Agent, in a Murine Model of Acute Viral Myocarditis, Journal of the American College of Cardiology, vol. 37, No. 6, pp. 1713-171 8, (2001); CAPLUS 2001 :382829.
Anandasabapathy et al., Innovative drug treatments for viral and autoimmune myocarditis., 1998, Journal of Clinical Pharmacology, vol. 38, No. 4, (Abstract Only).
Cleland et al., "What is the Optimal Medical Management of Ischaemic Heart Failure?", British Medical Bulletin, vol. 59, pp. 135-148, (2001).
Karliner, "Lysophospholipids and the Cardiovascular System," Biochimica et Biophysica Acta, vol. 1582, No. 1-3, pp. 216-221, (2002).
Llliom et al., Sphingosylphosphocholine is a Naturally Occurring Lipid Mediator in Blood Plasma: A Possible Role in Regulating Cardiac Function via Sphingolipid Receptors, Biochemical Journal, vol. 355, No. 1, pp. 189-197, (2001).
Lynch, "Lysophospholipid Receptor Nomenclature," Biochimica et Biophysica Acta, vol. 1582, No. 1-3, pp. 70-71, (2002).
Pyne et al., "Spingosine 1-phosphate Signaling via the Endothelial Differentiation Gene Family of G-Protein-Coupled Receptors," Pharmacology and Therapeutics, vol. 88, pp. 115-131, (2000).
Mandala, S., et al:. "Alteration of Lymphocyte Trafficking by Sphingosine-1-Phosphate Receptor Agonists", Science, vol. 296, pp. 346-349, Apr. 12, 2002.
Schmouder et al., "FTY720: Placebo-Controlled Study of the Effect on Cardiac Rate and Rhythm in Healthy Subjects", J Clin Pharmacol, vol. 46, pp. 895-904, (2006).

*Primary Examiner* — James D Anderson
*Assistant Examiner* — Meghan Finn
(74) *Attorney, Agent, or Firm* — Karen DeBenedictis; Jennifer Chapman; Cozette M. McAvoy

(57) ABSTRACT

The invention relates to the use of a sphingosine-1-phosphate receptor agonist in the treatment of heart diseases.

3 Claims, No Drawings

USE OF S1P RECEPTOR AGONISTS IN HEART DISEASES

The present invention relates to a new use for a sphingosine-1-phosphate (S1P) receptor agonist particularly in the treatment of heart diseases.

S1P receptor agonists are accelerating lymphocyte homing agents which elicit lymphopenia, resulting from a re-distribution, preferably reversible, of lymphocytes from circulation to secondary lymphatic tissue, without evoking a generalized immunosuppression. Naïve cells are sequestered; CD4 and CD8 T-cells and B-cells from the blood are stimulated to migrate into lymph nodes (LN) and Peyer's patches (PP), and thus for example infiltration of cells into transplanted organs is inhibited.

S1P receptor agonists are typically sphingosine analogues, such as 2-substituted 2-amino-propane-1,3-diol or 2-amino-propanol derivatives, e.g. a compound comprising a group of formula X

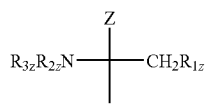

wherein

Z is H; $C_{1-6}$alkyl; $C_{2-6}$alkenyl; $C_{2-6}$alkynyl; phenyl; phenyl substituted by OH; $C_{1-6}$alkyl substituted by 1 to 3 substituents selected from the group consisting of halogen, $C_{3-8}$cycloalkyl, phenyl and phenyl substituted by OH; or $CH_2$—$R_{4z}$ where $R_{4z}$ is OH, acyloxy or a residue of formula (a)

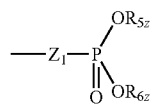

wherein $Z_1$ is a direct bond or O, preferably O; each of $R_{5z}$ and $R_{6z}$, and independently, is H, or $C_{1-4}$alkyl optionally substituted by 1, 2 or 3 halogen atoms;

$R_{1z}$ is OH, acyloxy or a residue of formula (a); and each of $R_{2z}$ and $R_{3z}$, independently, is H, $C_{1-4}$alkyl or acyl.

Group of formula X is a functional group attached as a terminal group to a moiety which may be hydrophilic or lipophilic and comprise one or more aliphatic, alicyclic, aromatic and/or heterocyclic residues, to the extent that the resulting molecule wherein at least one of Z and $R_{1z}$ is or comprises a residue of formula (a), signals as an agonist at one of more sphingosine-1-phosphate receptor.

S1P receptor agonists are compounds which signal as agonists at one or more spingosine-1 phosphate receptors, e.g. S1P1 to S1P8. Agonist binding to a S1P receptor may e.g. result in dissociation of intracellular heterotrimeric G-proteins into Gα-GTP and Gβγ-GTP, and/or increased phosphorylation of the agonist-occupied receptor and activation of downstream signaling pathways/kinases. The binding affinity of S1P receptor agonists may be measured as described at paragraph I. below. Preferred S1P receptor agonists are those targeting e.g. S1P2 and/or S1P3.

Examples of appropriate S1P receptor agonists are, for example:
Compounds as disclosed in EP627406A1, e.g. a compound of formula I

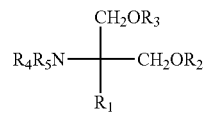

wherein $R_1$ is a straight- or branched ($C_{12-22}$)carbon chain
which may have in the chain a bond or a hetero atom selected from a double bond, a triple bond, O, S, $NR_6$, wherein $R_6$ is H, alkyl, aralkyl, acyl or alkoxycarbonyl, and carbonyl, and/or
which may have a substituent alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, nitro, halogen, amino, hydroxyimino, hydroxy or carboxy; or $R_1$ is
a phenylalkyl wherein alkyl is a straight- or branched ($C_{6-20}$) carbon chain; or
a phenylalkyl wherein alkyl is a straight- or branched ($C_{1-30}$) carbon chain wherein said phenylalkyl is substituted by
a straight- or branched ($C_{6-20}$) carbon chain optionally substituted by halogen,
a straight- or branched ($C_{6-20}$) alkoxy chain optionally substituted by halogen,
a straight- or branched ($C_{6-20}$) alkenyloxy,
phenylalkoxy, halophenylalkoxy, phenylalkoxyalkyl, phenoxyalkoxy or phenoxyalkyl,
cycloalkylalkyl substituted by $C_{5-20}$alkyl,
heteroarylalkyl substituted by $C_{5-20}$alkyl,
heterocyclic $C_{6-20}$alkyl or
heterocyclic alkyl substituted by $C_{2-20}$alkyl,
and wherein
the alkyl moiety may have
in the carbon chain, a bond or a heteroatom selected from a double bond, a triple bond, O, S, sulfinyl, sulfonyl, or $NR_6$, wherein $R_6$ is as defined above, and
as a substituent alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, nitro, halogen, amino, hydroxy or carboxy, and
each of $R_2$, $R_3$, $R_4$ and $R_5$, independently, is H, $C_{1-4}$alkyl or acyl
or a pharmaceutically acceptable salt thereof;
Compounds as disclosed in EP 1002792A1, e.g. a compound of formula II

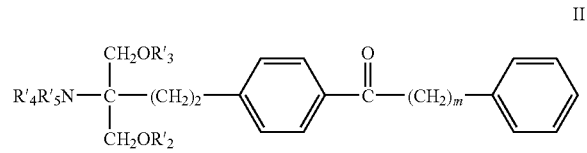

wherein m is 1 to 9 and each of $R'_2$, $R'_3$, $R'_4$ and $R'_5$, independently, is H, alkyl or acyl, or a pharmaceutically acceptable salt thereof;
Compounds as disclosed in EP0778263 A1, e.g. a compound of formula III

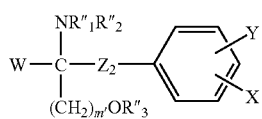

wherein W is H; $C_{1-6}$alkyl, $C_{2-8}$alkenyl or $C_{2-6}$alkynyl; unsubstituted or by OH substituted phenyl; $R''_4O(CH_2)_n$; or $C_{1-6}$alkyl substituted by 1 to 3 substituents selected from the group consisting of halogen, $C_{3-8}$cycloalkyl, phenyl and phenyl substituted by OH;

X is H or unsubstituted or substituted straight chain alkyl having a number p of carbon atoms or unsubstituted or substituted straight chain alkoxy having a number (p−1) of carbon atoms, e.g. substituted by 1 to 3 substitutents selected from the group consisting of $C_{1-6}$ alkyl, OH, $C_{1-6}$alkoxy, acyloxy, amino, $C_{1-6}$alkylamino, acylamino, oxo, halo$C_{1-6}$ alkyl, halogen, unsubstituted phenyl and phenyl substituted by 1 to 3 substituents selected from the group consisting of $C_{1-6}$alkyl, OH, $C_{1-6}$alkoxy, acyl, acyloxy, amino, $C_{1-6}$alkylamino, acylamino, halo$C_{1-6}$alkyl and halogen; Y is H, $C_{1-6}$alkyl, OH, $C_{1-6}$alkoxy, acyl, acyloxy, amino, $C_{1-6}$-alkylamino, acylamino, halo$C_{1-6}$alkyl or halogen, $Z_2$ is a single bond or a straight chain alkylene having a number or carbon atoms of q, each of p and q, independently, is an integer of 1 to 20, with the proviso of $6 \leq p+q \leq 23$, m' is 1, 2 or 3, n is 2 or 3, each of $R''_1$, $R''_2$, $R''_3$ and $R''_4$, independently, is H, $C_{1-4}$alkyl or acyl, or a pharmaceutically acceptable salt thereof, Compounds as disclosed in WO02/18395, e.g., a compound of formula IVa or IVb

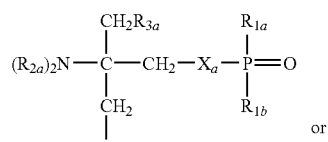

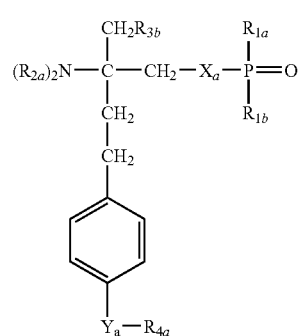

wherein $X_a$ is O, S, $NR_{1a}$ or a group $—(CH_2)_{na}—$, which group is unsubstituted or substituted by 1 to 4 halogen; $n_a$ is 1 or 2, $R_{1b}$ is H or $(C_{1-4})$alkyl, which alkyl is unsubstituted or substituted by halogen; $R_{1a}$ is H, OH, $(C_{1-4})$alkyl or $O(C_{1-4})$ alkyl wherein alkyl is unsubstituted or substituted by 1 to 3 halogen; $R_{1b}$ is H, OH or $(C_{1-4})$alkyl, wherein alkyl is unsubstituted or substituted by halogen; each $R_{2a}$ is independently selected from H or $(C_{1-4})$alkyl, which alkyl is unsubstituted or substituted by halogen; $R_{3a}$ is H, OH, halogen or $O(C_{1-4})$alkyl wherein alkyl is unsubstituted or substituted by halogen; and $R_{3b}$ is H, OH, halogen, $(C_{1-4})$alkyl wherein alkyl is unsubstituted or substituted by hydroxy, or $O(C_{1-4})$alkyl wherein alkyl is unsubstituted or substituted by halogen; $Y_a$ is $—CH_2—$, $—C(O)—$, $—CH(OH)—$, $—C(=NOH)—$, O or S, and $R_{4a}$ is $(C_{4-14})$alkyl or $(C_{4-14})$alkenyl;

or a pharmaceutically acceptable salt or hydrate thereof;

Compounds as disclosed in WO 02/076995, e.g. a compound of formula V

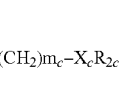

wherein
$m_c$ is 1, 2 or 3;
$X_o$ is O or a direct bond;
$R_{1c}$ is H; $C_{1-6}$ alkyl optionally substituted by OH, acyl, halogen, $C_{8-10}$cycloalkyl, phenyl or hydroxy-phenylene; $C_{2-6}$alkenyl; $C_{2-6}$alkynyl; or phenyl optionally substituted by OH;
$R_{2c}$ is

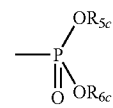

wherein $R_{5c}$ is H or $C_{1-4}$alkyl optionally substituted by 1, 2 of 3 halogen atoms, and $R_{6c}$ is H or $C_{1-4}$alkyl optionally substituted by halogen;

each of $R_{3c}$ and $R_{4c}$, independently, is H, $C_{1-4}$alkyl optionally substituted by halogen, or acyl, and $R_c$ is $C_{13-20}$alkyl which may optionally have in the chain an oxygen atom and which may optionally be substituted by nitro, halogen, amino, hydroxy or carboxy; or a residue of formula (a)

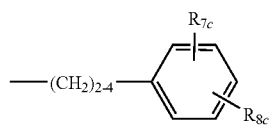

wherein $R_{7c}$ is H, $C_{1-4}$alkyl or $C_{1-4}$alkoxy, and $R_{8c}$ is substituted $C_{1-20}$alkanoyl, phenyl$C_{1-14}$alkyl wherein the $C_{1-14}$alkyl is optionally substituted by halogen or OH, cycloalkyl$C_{1-14}$alkoxy or phenyl$C_{1-14}$alkoxy wherein the cycloalkyl or phenyl ring is optionally substituted by halogen, $C_{1-4}$alkyl and/or $C_{1-4}$alkoxy, phenyl$C_{1-14}$ alkoxy-$C_{1-14}$alkyl, phenoxy $C_{1-14}$alkoxy or phenoxy $C_{1-14}$ alkyl, $R_c$ being also a residue of formula (a) wherein $R_{8c}$ is $C_{1-14}$alkoxy when $R_{1c}$ is $C_{1-4}$alkyl, $C_{2-6}$alkenyl or $C_{2-6}$alkynyl, or a compound of formula VI

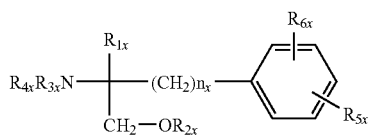

wherein
$n_x$ is 2, 3 or 4
$R_{1x}$ is H; $C_{1-6}$alkyl optionally substituted by OH, acyl, halogen, cycloalkyl, phenyl or hydroxy-phenylene; $C_{2-6}$alkenyl; $C_{2-6}$alkynyl; or phenyl optionally substituted by OH;
$R_{2x}$ is H, $C_{1-4}$alkyl or acyl
each of $R_{3x}$ and $R_{4x}$, independently is H, $C_{1-4}$alkyl optionally substituted by halogen or acyl,
$R_{3x}$ is H, $C_{1-4}$alkyl or $C_{1-4}$alkoxy, and
$R_{6x}$ is $C_{1-20}$alkanoyl substituted by cycloalkyl; cyloalkyl$C_{1-14}$alkoxy wherein the cycloalkyl ring is optionally substituted by halogen, $C_{1-4}$alkyl and/or $C_{1-4}$alkoxy; phenyl $C_{1-14}$alkoxy wherein the phenyl ring is optionally substituted by halogen, $C_{1-4}$alkyl and/or $C_{1-4}$alkoxy,
$R_{6x}$ being also $C_{4-14}$alkoxy when $R_{1x}$ is $C_{2-4}$alkyl substituted by OH, or pentyloxy or hexyloxy when $R_{1x}$ is $C_{1-4}$akyl,
provided that $R_{6x}$ is other than phenyl-butylenoxy when either $R_{5x}$ is H or $R_{1x}$ is methyl,
or a pharmaceutically acceptable salt thereof;

Compounds as disclosed in WO02/06268A1, e.g. a compound of formula VII

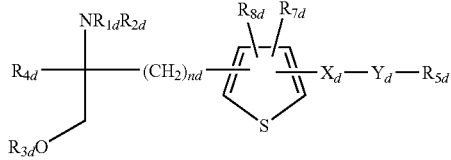

wherein each of $R_{1d}$ and $R_{2d}$, independently, is H or an amino-protecting group;
$R_{3d}$ is hydrogen, a hydroxy-protecting group or a residue of formula

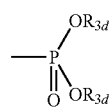

$R_{4d}$ is lower alkyl;
$n_d$ is an integer of 1 to 6;
$X_d$ is ethylene, vinylene, ethynylene, a group having a formula —D—CH$_2$— (where D is carbonyl, —CH(OH)—, O, S or N), aryl or aryl substituted by up to three substituents selected from group a as defined hereinafter;
$Y_d$ is single bond, $C_{1-10}$alkylene, $C_{1-10}$alkylene which is substituted by up to three substituents selected from groups a and b, $C_{1-10}$alkylene having O or S in the middle or end of the carbon chain, or $C_{1-10}$alkylene having O or S in the middle or end of the carbon chain which is substituted by up to three substituents selected from groups a and b;
$R_{5d}$ is hydrogen, cycloalkyl, aryl, heterocycle, cycloalkyl substituted by up to three substituents selected from groups a and b, aryl substituted by up to three substituents selected from groups a and b, or heterocycle substituted by up to three substituents selected from groups a and h;
each of $R_{6d}$ and $R_{7d}$, independently, is H or a substituent selected from group a;
each of $R_{8d}$ and $R_{9d}$, independently, is H or $C_{1-4}$alkyl optionally substituted by halogen;
<group a> is halogen, lower alkyl, halogeno lower alkyl, lower alkoxy, lower alkylthio, carboxyl, lower alkoxycarbonyl, hydroxy, lower aliphatic acyl, amino, mono-lower alkylamino, di-lower alkylamino, lower aliphatic acylamino, cyano or nitro; and
<group b> is cycloalkyl, aryl, heterocycle, each being optionally substituted by up to three substituents selected from group a;
with the proviso that when is hydrogen, is a either a single bond or linear $C_{1-10}$ alkylene, or a pharmacologically acceptable salt or ester thereof;

Compounds as disclosed in JP-14316985 (JP2002318985), e.g. a compound of formula VIII:

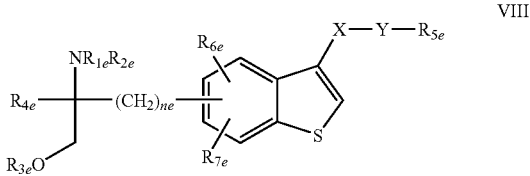

wherein $R_{1e}$, $R_{2e}$, $R_{3e}$, $R_{4e}$, $R_{5e}$, $R_{6e}$, $R_{7e}$, $n_e$, $X_e$ and $Y_e$ are as disclosed in JP-14316985;
or a pharmacologically acceptable salt or ester thereof;

Compounds as disclosed in WO 03/29184 and WO 03/29205, e.g. compounds of formula IX

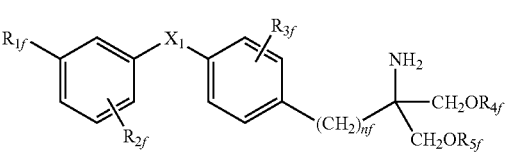

wherein $X_1$ is O or S, and $R_{1f}$, $R_{2f}$, $R_{3f}$ and $n_f$ are as disclosed in WO 03/29184 and O3/29205, each of $R_{4f}$ and $R_{5f}$, independently is H or a residue of formula

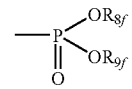

wherein each of $R_{8f}$ and $R_{9f}$, independently, is H or $C_{1-4}$alkyl optionally substituted by halogen; e.g. 2-amino-2-[4-(3-benzyloxyphenoxy)-2-chlorophenyl]propyl-1,3-propane-diol or 2-amino-2-[4-(benzyloxyphenylthio)-2-chlorophenyl]propyl-1,3-propane-diol, or a pharmacological salt thereof.

In each case where citations of patent applications are given, the subject matter relating to the compounds is hereby incorporated into the present application by reference.

Acyl may be a residue $R_y$—CO— wherein $R_y$ is $C_{1-6}$alkyl, $C_{3-6}$cycloalkyl, phenyl or phenyl-$C_{1-4}$alkyl. Unless otherwise stated, alkyl, alkoxy, alkenyl or alkynyl may be straight or branched.

When in the compounds of formula I the carbon chain as $R_1$ is substituted, it is preferably substituted by halogen, nitro, amino, hydroxy or carboxy. When the carbon chain is interrupted by an optionally substituted phenylene, the carbon chain is preferably unsubstituted. When the phenylene moiety is substituted, it is preferably substituted by halogen, nitro, amino, methoxy, hydroxy or carboxy.

Preferred compounds of formula I are those wherein $R_1$ is $C_{13-20}$alkyl, optionally substituted by nitro, halogen, amino, hydroxy or carboxy, and, more preferably those wherein $R_1$ is phenylalkyl substituted by $C_{6-14}$-alkyl chain optionally substituted by halogen and the alkyl moiety is a $C_{1-6}$alkyl optionally substituted by hydroxy. More preferably, $R_1$ is phenyl-$C_{1-6}$alkyl substituted on the phenyl by a straight or branched, preferably straight, $C_{6-14}$alkyl chain. The $C_{6-14}$alkyl chain may be in ortho, meta or para, preferably in para.

Preferably each of $R_2$ to $R_5$ is H.

A preferred compound of formula I is 2-amino-2-tetradecyl-1,3-propanediol. A particularly preferred S1P receptor agonist of formula I is FTY720, i.e. 2-amino-2-[2-(4-octylphenyl) ethyl]propane-1,3-diol in free form or in a pharmaceutically acceptable salt form (referred to hereinafter as Compound A), e.g. the hydrochloride, as shown:

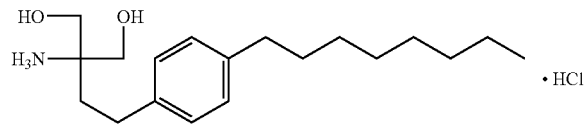

A preferred compound of formula II is the one wherein each of $R'_2$ to $R'_5$ is H and m is 4, i.e. 2-amino-2-(2-[4-(1-oxo-5-phenylpentyl)phenyl]ethyl)propane-1,3-diol, in free form or in pharmaceutically acceptable salt form (referred to hereinafter as Compound B), e.g the hydrochloride.

A preferred compound of formula III is the one wherein W is $CH_3$, each of $R''_1$ to $R''_3$ is H, $Z_2$ is ethylene, X is heptyloxy and Y is H, i.e. 2-amino-4-(4-heptyloxyphenyl)-2-methylbutanol, in free form or in pharmaceutically acceptable salt form (referred to hereinafter as Compound C), e.g. the hydrochloride. The R-enantiomer is particularly preferred.

A preferred compound of formula IVa is the FTY720-phosphate ($R_{2a}$ is H, $R_{3a}$ is OH, $X_a$ is O, $R_{1a}$ and $R_{1b}$ are OH). A preferred compound of formula IVb is the Compound C-phosphate ($R_{2b}$ is H, $R_{3b}$ is OH, $X_a$ is O, $R_{1a}$ and $R_{1b}$ are OH, $Y_a$ is O and $R_{4a}$ is heptyl). A preferred compound of formula V is Compound B-phosphate.

A preferred compound of formula V is phosphoric acid mono-[(R)-2-amino-2-methyl-4-(4-pentyloxy-phenyl)-butyl]ester.

A preferred compound of formula VIII is (2R)-2-amino-4-[3-(4-cyclohexyloxybutyl)-benzo[b]thien-6-yl]-2-methylbutan-1-ol.

When the compounds of formulae I to IX have one or more asymmetric centers in the molecule, the present invention is to be understood as embracing the various optical isomers, as well as racemates, diastereoisomers and mixtures thereof are embraced. Compounds of formula III or IVb, when the carbon atom bearing the amino group is asymmetric, have preferably the R-configuration at this carbon atom.

Examples of pharmaceutically acceptable salts of the compounds of the formulae I to IX include salts with inorganic acids, such as hydrochloride, hydrobromide and sulfate, salts with organic acids, such as acetate, fumarate, maleate, benzoate, citrate, malate, methanesulfonafe and benzenesulfonate salts, or, when appropriate, salts with metals such as sodium, potassium, calcium and aluminium, salts with amines, such as triethylamine and salts with dibasic amino acids, such as lysine. The compounds and salts of the methods of the present invention encompass hydrate and solvate forms.

The S1P receptor agonists have, on the basis of observed activity, e.g. homing of lymphocytes, e.g. as described in EP627406A1 or U.S. Pat. No. 6,004,565, been found to be useful e.g. as immunosuppressant, e.g. in the treatment of acute allograft rejection.

It has now been found that S1P receptor agonists have a beneficial effect in heart diseases, e.g. in chronic heart failure, congestive heart failure, complications of cardiovascular surgery, peri-operative hypertension, unstable angina or acute myocardial infarction.

Chronic heart failure is a clinical syndrome characterized by distinctive symptoms and signs resulting from disturbances in cardiac output, e.g. inadequate for the body's needs. It is often associated with other changes such as cardiac hypertrophy and myocardial ischemia. Congestive heart failure (CHF), or heart failure, is a condition in which the heart cannot pump enough blood to the body's other organs. As blood flow out of the heart slows, blood returning to the heart through the veins backs up, causing congestion in the tissues.

In accordance with the particular findings of the present invention, there is provided;

1.1 A method for treating chronic heart failure in a subject in need thereof comprising administering to said subject a therapeutically effective amount of a S1P receptor agonist;

1.2 A method for improving heart energy efficiency and/or reducing its oxygen needs in a subject in need thereof comprising administering to said subject a therapeutically effective amount of a S1P receptor agonist;

1.3 A method for improving cardiac output in a subject in need thereof comprising administering to said subject a therapeutically effective amount of a S1P receptor agonist;

1.4 A method for treating arrhythmia or tachyarrhythmia, e.g. atrial fibrillation, atrial flutter or sinus ventricular tachycardia, in a subject in need thereof comprising administering to said subject a therapeutically effective amount of a S1P receptor agonist;

1.5 A method for treating congestive heart failure in a subject in need thereof comprising administering to said subject a therapeutically effective amount of a S1P receptor agonist;

The method of the invention is also appropriate for patients with acutely decompensated congestive heart failure and patients with pre-existing arrythmias.

1.6 A method for treating complications of cardiovascular surgery, e.g. peri-operative hypertension, in a subject in need thereof comprising administering to said subject a therapeutically effective amount of a S1P receptor agonist;

1.7 A method for treating unstable angina in a subject in need thereof comprising administering to said subject a therapeutically effective amount of a S1P receptor agonist;

1.8 A method for treating acute myocardial infarction In a subject in need thereof comprising administering to said subject a therapeutically effective amount of a S1P receptor agonist.

2. A S1P receptor agonist a compound of formula I or a pharmaceutically acceptable salt thereof, for use in a method as defined under 1.1 to 1.8 above; or 3. A S1P receptor agonist, e.g. a compound of formula I or a pharmaceutically acceptable salt thereof, for use in the preparation of a pharmaceutical composition for use in a method as defined under 1.1 to 1.8 above; or 4. A pharmaceutical composition for use in a method as defined under 1.1 to 1.8 above comprising a S1P receptor agonist, e.g. a compound of formula I or a pharmaceutically acceptable salt thereof, together with one or more pharmaceutically acceptable diluents or carriers therefor, Utility of the S1P receptor agonists, e.g. in the treatment of heart diseases, as hereinabove specified, may be demonstrated in animal test methods as well as in clinic, for example in accordance with the methods hereinafter described.

A. Binding Affinity of S1P Receptor Agonists to Individual Human S1P Receptors May be Determined in Following Assays:

Transient Transfection of Human S1P Receptors into HEK293 Cells

S1P receptors and $G_i$ proteins are cloned, and equal amounts of 4 cDNAs for the S1P receptor, $G_1$-$\alpha$, $G_1$-$\beta$ and $G_1$-$\gamma$ are mixed and used to transfect monolayers of HEK293 cells using the calcium phosphate precipitate method (M. Wigler et al., Cell, 1977; 11; 223 and D. S. Im et al., Mol. Pharmacol. 2000; 57; 753). Briefly, a DNA mixture containing 25 µg of DNA and 0.25 M CaCl is added to HEPES-buffered 2 mM $Na_2HPO_4$. Subconfluent monolayers of HEK293 cells are poisoned with 25 mM chloroquine, and the DNA precipitate is then applied to the cells. After 4 h, the monolayers are washed with phosphate-buffered saline and refed media (90% 1:1 Dulbecco's modified essential media (DMEM):F–12+10% fetal bovine serum). The cells are harvested 48-72 h after addition of the DNA by scraping in HUE buffer (in mM; 20 HEPES, 5 $MgCl_2$, 1 EDTA, pH 7.4) containing 10% sucrose on ice, and disrupted using a Pounce homogenizer. After centrifugation at 800×g, the supernatant is diluted with HME without sucrose and cenfrifuged at 100,000×g for 1 h. The resulting pellet is rehomogenized and centrifuged a second hour at 100,000×g. This crude membrane pellet is resuspended in HME with sucrose, aliquoted, and snap-frozen by immersion in liquid nitrogen. The membranes are stored at 70° C. Protein concentration is determined spectroscopically by Bradford protein assay.

GTPγS Binding Assay Using S1P Receptor/HEK293 Membrane Preparations

GTPγS binding experiments are performed as described by D S. Im et al., Mol. Pharmacol. 2000; 57:753. Ligand-mediated GTPγS binding to G-proteins is measured in GTP binding buffer (in mM: 50 HEPES, 100 NaCl, 10 $MgCl_2$, pH 7.5) using 25 µg of a membrane preparation from transiently transfected HEK293 cells. Ligand is added to membranes in the presence of 10 µM GDP and 0.1 nM [$^{35}$S]GTPγS (1200 Cl/mmol) and incubated at 30+ C. for 30 min. Bound GTPγS is separated from unbound using the Brandel harvester (Gaithersburg, Md.) and counted with a liquid scintillation counter.

B. In Vivo

The effect of a S1P receptor agonist, e.g. a compound of formula I on chronic heart failure is tested in rabbits where heart failure is induced as a consequence of a large myocardial infarction (R P. Hof et al. J. Cardiovasc. Pharmacol., 1991, 18,361-368). The changes of atrial natriuretic factor or baroflex sensitivity are a reliable indicator of the status of the heart failure in this animal model. When administered i.v. at a dose of from 0.1 to 10 mg/kg, a S1P receptor agonist, e.g. the compounds of formula I, e.g. Compound A, have a beneficial effect on the heart failure.

C. Clinical Trial

Patients with class IV congestive heart failure are selected: they have elevated intracardiac filling pressures (orthopnea, abdominal discomfort attributed to hepato-splenic congestion, peripheral edema, ascites, raies and jugular venous distension) and inadequate peripheral perfusion. Patients receive a daily dose of the S1P receptor agonist to be tested, e.g. Compound A in free form or a pharmaceutical acceptable salt thereof, e.g. orally, during 2 or 4 weeks or 3 months. The dose may be escalated if necessary. Patients are followed-up for 6 months. Following data are collected during hospitalization and the 6 month follow-up: blood pressure, weight, electrocardiogram, echocardiogram, serum electrolytes, natriuretic hormone profile and exercise stress tests.

A beneficial effect is observed.

Daily dosages required in practicing the method of the present invention will vary depending upon, for example, the compound used, the host, the mode of administration, the severity of the condition to be treated. A preferred daily dosage range is about from 0.03 to 2.5 mg/kg per day as a single dose or in divided doses. Suitable daily dosages for patients are on the order of from e.g. 0.5 to 50 mg p.o. Suitable unit dosage forms for oral administration comprise from ca. 0.1 to 25 mg active ingredient, e.g. FTY720, e.g. in hydrochloride form, together with one or more pharmaceutically acceptable diluents or carriers therefor. As an alternative, the S1P receptor agonist may also be administered twice or three times a week, e.g. at a dosage as indicated above.

The S1P receptor agonist may be administered by any conventional route, in particular enterally, e.g. orally, for example in the form of solutions for drinking, tablets or capsules or parenteral, for example in the form of injectable solutions or suspensions. Pharmaceutical compositions comprising a S1P receptor agonist, e.g. a compound of formula I may be manufactured in conventional manner, e.g. as described in EP-A1-627,406 or in EP-A1-1,002,792.

The S1P receptor agonists may be administered as the sole ingredient or together with other drugs, e.g. an angiotensin converting enzyme inhibitor, e.g. benazepril, captopril, quinapril, ramipril, enalapril, linisopril or moexipril, an angiotensin II receptor antagonist, e.g. valsartan, losartan, irbesartan, eprosartan, forasartan, olmesartan, ripisartan, saprisartan, candesartan, tasosartan or telmisartan, a synthetic form of B-type natriuretic peptide (BMP) or other human B-type natriuretic peptide, e.g. nesiritide, other drugs used in patients with heart failure, e.g. digoxin or digitalis preparations, a β-blocker, e.g. propanoiol, atenolol, a β-adrenergic receptor agonist, e.g. salbutamol, an α-2 receptor agonist, e.g. dexmetomidine, a calcium antagonist, e.g. clinidipine, or a diuretic, e.g. hydrochlorothiazide or spironolactone.

Where the S1P receptor agonists are administered in conjunction with other drugs, dosages of the co-administered compound will of course vary depending on the type of co-drug employed, on the specific drug employed, on the condition to be treated, and so forth. The terms "co-administration" or "combined administration" or the like as utilised herein are meant to encompass administration of the selected therapeutic agents to a single patient, and are intended to include treatment regimens m which the agents are not necessarily administered by the same route of administration or at the same time.

In accordance with the foregoing the present invention provides in a yet further aspect:

5. A pharmaceutical combination comprising a) a first agent which is a S1P receptor agonist, e.g. a compound of formula I, e.g. FTY720, or Compound B or C or a compound of formula V or VIII, or a phosphate thereof, or a pharmaceutically acceptable salt thereof, and b) a co-agent, e.g. a second drug agent as defined above.
6. A method as defined above comprising co-administration, e.g. concomitantly or in sequence, of a therapeutically effective amount of a S1P receptor agonist, e.g. a compound of formula I, e.g. FTY720, or Compound B or C, or a compound of formula V or VIII, or a phosphate thereof, or a pharmaceutically acceptable salt thereof, and a second drug substance, e.g. as indicated above.

S1P receptor agonists are well tolerated at dosages required for use in accordance with the present invention. For example, FTY720 has an acute $LD_{50}$ >10 mg/kg p.o. in rats and monkeys.

The administration of a pharmaceutical combination of the invention results in a beneficial effect, e.g. a synergistic therapeutic effect, less side-effects or an improved quality of life compared to a monotherapy.

The invention claimed is:

1. A method for treating chronic heart failure or congestive heart failure in a subject in need thereof, comprising administering to said subject a therapeutically effective amount of 2-amino-2-[2-(4-octylphenyl)ethyl]propane-1,3-diol (FTY720) in free form or in a pharmaceutically acceptable salt form, or FTY720-phosphate.

2. The method of claim 1, comprising administering to said subject a therapeutically effective amount of the hydrochloride salt of FTY720.

3. The method of claim 1, wherein said patient is suffering from acutely decompensated congestive heart failure.

* * * * *